United States Patent
Miller et al.

(10) Patent No.: US 10,131,608 B2
(45) Date of Patent: Nov. 20, 2018

(54) HYDROFORMYLATION PROCESS

(71) Applicant: Dow Technology Investments LLC, Midland, MI (US)

(72) Inventors: Glenn A. Miller, South Charleston, WV (US); Thomas C. Eisenschmid, South Charleston, WV (US); Michael A. Brammer, Freeport, TX (US); Michael C. Becker, Dickinson, TX (US); Rick B. Watson, Missouri City, TX (US)

(73) Assignee: Dow Technology Investments LLC, Midland, MI (US)

( * ) Notice: Subject to any disclaimer, the term of this patent is extended or adjusted under 35 U.S.C. 154(b) by 59 days.

(21) Appl. No.: 15/114,191

(22) PCT Filed: Mar. 10, 2015

(86) PCT No.: PCT/US2015/019560
§ 371 (c)(1),
(2) Date: Jul. 26, 2016

(87) PCT Pub. No.: WO2015/153070
PCT Pub. Date: Oct. 8, 2015

(65) Prior Publication Data
US 2017/0233322 A1    Aug. 17, 2017

Related U.S. Application Data

(60) Provisional application No. 61/972,628, filed on Mar. 31, 2014.

(51) Int. Cl.
*C07C 45/00* (2006.01)
*C07C 45/80* (2006.01)
*C07C 45/50* (2006.01)

(52) U.S. Cl.
CPC .............. *C07C 45/80* (2013.01); *C07C 45/50* (2013.01)

(58) Field of Classification Search
None
See application file for complete search history.

(56) References Cited

U.S. PATENT DOCUMENTS

| | | |
|---|---|---|
| 3,415,906 A | 12/1968 | Shepard et al. |
| 3,527,809 A | 9/1970 | Pruett et al. |
| 4,148,830 A | 4/1979 | Pruett et al. |
| 4,247,486 A | 1/1981 | Brewester et al. |
| 4,487,972 A | 12/1984 | Haag et al. |
| 4,518,809 A | 5/1985 | Forster et al. |
| 4,528,403 A | 7/1985 | Tano et al. |
| 4,567,302 A | 1/1986 | Sivaramakrishnan |
| 4,567,306 A | 1/1986 | Dennis et al. |
| 4,593,127 A | 6/1986 | Bunning et al. |
| 4,599,206 A | 7/1986 | Billig et al. |
| 4,668,651 A | 5/1987 | Billig et al. |
| 4,717,775 A | 1/1988 | Billig et al. |
| 4,737,588 A | 4/1988 | Billig et al. |
| 4,748,261 A | 5/1988 | Billig et al. |
| 4,769,498 A | 9/1988 | Billig et al. |
| 4,774,361 A | 9/1988 | Maher et al. |
| 4,835,299 A | 5/1989 | Maher et al. |
| 4,885,401 A | 12/1989 | Billig et al. |
| 5,113,022 A | 5/1992 | Abatjoglou et al. |
| 5,179,055 A | 1/1993 | Wink et al. |
| 5,183,943 A | 2/1993 | Bryant et al. |
| 5,202,297 A | 4/1993 | Lorz et al. |
| 5,235,113 A | 8/1993 | Sato et al. |
| 5,264,616 A | 11/1993 | Roeper et al. |
| 5,288,918 A | 2/1994 | Maher et al. |
| 5,312,996 A | 5/1994 | Packett |
| 5,360,938 A | 11/1994 | Babin et al. |
| 5,364,950 A | 11/1994 | Babin et al. |
| 5,391,801 A | 2/1995 | Sato et al. |
| 5,430,194 A | 7/1995 | Barner et al. |
| 5,449,653 A | 9/1995 | Briggs et al. |
| 5,491,266 A | 2/1996 | Babin et al. |
| 5,527,950 A | 6/1996 | Hansen et al. |
| 5,681,473 A | 10/1997 | Miller et al. |
| 5,710,344 A | 1/1998 | Breikss et al. |
| 5,731,472 A | 3/1998 | Leung et al. |
| 5,741,944 A | 4/1998 | Bryant et al. |
| 5,744,649 A | 4/1998 | Bryant et al. |
| 5,763,677 A * | 6/1998 | Bryant ..................... B01J 19/18 568/451 |
| 5,763,679 A | 6/1998 | Nicholson et al. |
| 5,929,289 A | 7/1999 | Abatjoglou et al. |
| 6,153,800 A | 11/2000 | Gelling et al. |
| 6,265,620 B1 | 7/2001 | Urata et al. |
| 6,440,891 B1 | 8/2002 | Maas et al. |
| 6,763,679 B1 | 7/2004 | Leitch et al. |
| 7,009,068 B2 | 3/2006 | Schmutzler et al. |
| 7,145,042 B2 | 12/2006 | Volland et al. |
| 7,196,230 B2 | 3/2007 | Peng et al. |
| 7,223,374 B2 | 5/2007 | Magna et al. |
| 7,351,339 B2 | 4/2008 | Maase et al. |
| 7,495,134 B2 | 2/2009 | Hess et al. |
| 7,586,010 B2 | 9/2009 | Liu et al. |
| 7,615,645 B2 | 11/2009 | Volland et al. |
| 7,674,937 B2 | 3/2010 | Tolleson et al. |
| 7,872,156 B2 | 1/2011 | Liu et al. |
| 8,003,816 B2 | 8/2011 | Selent et al. |
| 8,110,709 B2 | 2/2012 | Papp et al. |
| 8,461,394 B2 | 6/2013 | Lueken et al. |
| 8,884,072 B2 | 11/2014 | Miller et al. |
| 9,174,907 B2 | 11/2015 | Brammer et al. |
| 2014/0051568 A1 | 2/2014 | Eisenschmid et al. |

FOREIGN PATENT DOCUMENTS

| IN | 188332 B | 9/2002 |
|---|---|---|
| WO | 1988008835 A1 | 11/1988 |

OTHER PUBLICATIONS

PCT/US2015/019560, International Search Report and Written Opinion dated Jun. 8, 2015.
PCT/US2015/019560, International Preliminary Report on Patentability dated Oct. 4, 2016.

* cited by examiner

*Primary Examiner* — Ana Z Muresan

(57) ABSTRACT

A hydroformylation process wherein a water-soluble amine is contacted with the reaction fluid, liquid from the reactor is sent to an extraction zone, and a neutralized phosphorus acidic compound is at least partially removed from the extraction zone.

11 Claims, No Drawings

HYDROFORMYLATION PROCESS

BACKGROUND OF THE INVENTION

The invention relates to a hydroformylation process.

It is known that aldehydes can be produced by reacting an olefinically unsaturated compound with carbon monoxide and hydrogen in the presence of a rhodium-organophosphite ligand complex catalyst, and that preferred processes involve continuous hydroformylation and recycling of the catalyst solution as is disclosed, for example, in U.S. Pat. Nos. 4,148,830; 4,717,775 and 4,769,498. Such aldehydes have a wide range of known utility and are useful, for example, as intermediates for hydrogenation to aliphatic alcohols, for aldol condensation to produce plasticizers, and for oxidation to produce aliphatic acids.

Notwithstanding the benefits of such rhodium-organophosphorous ligand complex catalyzed liquid recycle hydroformylation processes, stabilization of the catalyst and organophosphorous ligand is a primary concern. Loss of catalyst or catalytic activity due to undesirable reactions of the highly expensive rhodium catalysts are detrimental to the production of the desired aldehyde. Degradation of the organophosphorous ligand employed during the hydroformylation process can lead to the formation of detrimental species, such as poisoning organophosphorous compounds, inhibitors, or acidic by-products, that can lower the catalytic activity of the rhodium catalyst. Production costs of the aldehyde product increase when productivity of the catalyst decreases.

Hydrolytic instability of hydrolyzable organophosphite ligands is a major cause of ligand degradation and catalyst deactivation for rhodium-organophosphorous ligand complex catalyzed hydroformylation processes. All organophosphites are susceptible to hydrolysis to some degree, the rate of hydrolysis generally being dependent on the stereochemical nature of the organophosphite. Typically, the bulkier the steric environment around the phosphorus atom, the slower the hydrolysis rate. For example, tertiary triorganophosphites, such as triphenylphosphite, are more susceptible to hydrolysis than diorganophosphites, such as those disclosed in U.S. Pat. No. 4,737,588, and organopolyphosphites such as those disclosed in U.S. Pat. No. 4,748,261 and U.S. Pat. No. 4,769,498. All such hydrolysis reactions invariably produce phosphorus acidic compounds that catalyze the hydrolysis reactions. For example, the hydrolysis of a tertiary organophosphite produces a phosphonic acid diester, which is hydrolyzable to a phosphonic acid monoester, which in turn is hydrolyzable to $H_3PO_3$ (phosphorous acid). Moreover, hydrolysis of the ancillary products of side reactions, such as between a phosphonic acid diester and the aldehyde or between certain organophosphite ligands and an aldehyde, can lead to production of undesirable strong aldehyde acids, e.g., n-$C_3H_7CH(OH)P(O)(OH)_2$.

Even highly desirable sterically-hindered organobisphosphites that are not very hydrolyzable can react with the aldehyde product to form poisoning organophosphites, e.g., organomonophosphites, which are catalytic inhibitors and which are far more susceptible to hydrolysis and the formation of such aldehyde acid by-products, e.g., hydroxy alkyl phosphonic acids, as shown, for example, in U.S. Pat. No. 5,288,918 and U.S. Pat. No. 5,364,950. Further, the hydrolysis of organophosphite ligands may be considered to be autocatalytic in view of the production of such phosphorus acidic compounds, e.g., $H_3PO_3$, aldehyde acids, such as hydroxy alkyl phosphonic acids, $H_3PO_4$ and the like, and if left unchecked the catalyst system of a continuous liquid recycle hydroformylation process will become more and more acidic over time. The eventual build-up of an unacceptable amount of phosphorus acidic materials can cause the total destruction of the organophosphite present, thereby rendering the hydroformylation catalyst totally ineffective (deactivated) and the valuable rhodium metal susceptible to loss, e.g., due to precipitation and/or deposition on the walls of the reactor. For example, in U.S. Pat. No. 5,741,944, a buffered extractor can be used to remove acidic species as they are formed, but this extraction is done outside of the reactor system and can be overwhelmed in some cases. The acid mitigation does not occur under the high temperature and multiple hour residence time conditions of the reactor, thus some degradation may occur before the acid neutralization can occur. Also, sodium-based oxy-acid buffers have shown a tendency to deposit Na-based solids (primarily of neutralized acidic species) that can cause severe operating difficulties, including plant shutdowns.

Numerous methods have been proposed to maintain catalyst and/or organophosphite ligand stability. For instance, U.S. Pat. No. 5,288,918 suggests adding to the reaction zone a catalytic activity enhancing additive, such as water and/or a weakly acidic compound; U.S. Pat. No. 5,364,950 suggests adding to the reaction zone an epoxide to stabilize the organophosphite ligand; and U.S. Pat. No. 5,741,944 teaches adding an oxyacid salt buffer to the extractor, optionally with amine additives, to remove acidic species from the catalyst solution. A further enhancement of the buffered extractor is taught in WO 2012/064586, wherein a water-washing step is added to remove metal salts derived from the oxyacid salt buffer prior to recycling the catalyst solution to the reaction zone.

U.S. Pat. No. 5,744,649 teaches extraction and removal of the acidic species using unbuffered water, i.e., a "water-only extractor." However, maintaining the desired effective pH of the catalyst solution requires a very large flow of de-ionized water, which results in elevated product, ligand and catalyst loss due to entrainment or dissolution in the water phase. Amine additives optionally may be used for the purpose of rejuvenating deactivated catalyst or for preventing acidic impurities from complexing the active catalyst. The amines may also act to "deliver" the neutralized acid to the water-only extractor. It is taught that the amine should preferentially partition into the organic phase and thus substantially not enter into the aqueous phase. '649 specifically teaches that "the acidic materials are extracted into the water as disclosed herein as opposed to merely being scavenged and/or neutralized and allowed to remain in the reaction medium." To be effective in the above roles, relatively high levels (as high as 10 wt %) of the amine additives are needed. However, such high levels of amines can cause issues with the extractor phase separation, such as generating emulsions and increasing catalytic metal losses.

U.S. Pat. No. 4,567,306 teaches the use of amines to neutralize acidic species to maintain catalyst activity. It does not teach what happens to these amines (other than being volatilized out with the product) and does not teach how to remove the salts so formed. Eventually, the salts will build up until they precipitate.

U.S. Pat. No. 8,110,709 claims the use of amines to trap acidic impurities, then the use of an ion exchange column to remove the resulting amine salts. Similarly, U.S. Pat. No. 7,495,134 teaches the addition of secondary amine additives to precipitate acidic salts, which are removed by filtration.

Some hydrolysis of undesirable phosphorous species is acceptable. U.S. Pat. No. 5,288,918 teaches that it is important to hydrolyze some ligand degradation products that act as catalyst poisons or inhibitors. This can be done without significant hydrolysis of the desirable hydrolyzable ligand by careful control of the effective pH of the system, since these ligand degradation species decompose faster than the desirable ligands in specific pH ranges. U.S. Pat. No. 5,741,944 teaches that the preferred pH range of the acid removal zone is 4.5 to 7.5 and most preferably is between 5.6 and 7.0. If the effective pH is lower than that, hydrolysis of all phosphorous esters occurs; however, if it is higher than that, then the catalyst poison hydrolysis rate is too slow and the catalyst becomes poisoned.

Prior art buffered extractors have been based on metal salts of oxyacids such as $Na_xH_yPO4$. The buffer is typically preformed and fed at a concentration of >0.1 mmol/L to a countercurrent extractor where the acids are neutralized and removed under carefully controlled pH conditions. It was presumed in the prior art that the control of the pH in the aqueous buffer phase corresponds to an effective acidity control in the reaction zone. Unfortunately, despite the teachings in WO 2012/064586, a slow buildup of fouling materials based on sodium salts has been observed. Adding amines to water at these concentrations without an oxyacid salt buffer present gives unacceptably high pH values and heavies formation in the reaction fluid. To have sufficient buffer capacity, high levels of amines such as pyridine, trialkylamines, and the like gave unacceptably high aqueous pH values (>9).

Notwithstanding the value of the teachings of the prior art, the search for alternative methods and an even better and more efficient means for stabilizing the rhodium catalyst and organophosphite ligand employed remains an ongoing activity. It would be desirable to have a process to reduce or eliminate highly acidic species in the hydroformylation reaction zone in order to minimize ligand degradation while reducing poisoning phosphite levels without the fouling observed with metal salt buffers.

SUMMARY OF THE INVENTION

The invention is such a process comprising: (1) conducting in a reaction zone a hydroformylation reaction employing a reaction fluid comprising (a) a phosphorus acidic compound, (b) a metal-organophosphorus ligand complex catalyst that comprises a metal of Group 8, 9 or 10 complexed with an organophosphorous ligand, and, optionally, (c) free organophosphorus ligand; (2) contacting at least a portion of the reaction fluid with a water-soluble amine to neutralize at least some amount of the phosphorus acidic compound and to form a neutralized phosphorus acidic compound; (3) at least partially separating in an extraction zone at least one neutralized phosphorus acidic compound from the reaction fluid; and (4) removing the neutralized phosphorus acidic compound from the extraction zone via an extraction zone aqueous effluent stream; with the proviso that the amount of amine is such that the concentration of the amine in the reaction zone is not more than 0.075 mmoles per liter of hydroformylation reaction fluid.

Surprisingly, the process of the invention provides a way to control ligand degradation without increased heavies formation, and with reduced fouling compared to processes that employ metal salt buffers.

DETAILED DESCRIPTION OF THE INVENTION

The disclosed process comprises contacting a water-soluble amine with a hydroformylation reaction fluid. The reaction fluid comprises (1) a phosphorus acidic compound, (2) a metal-organophosphorus ligand complex catalyst that comprises a metal complexed with an organophosphorous ligand, and, optionally, (3) free organophosphorus ligand. The reaction fluid can be generated in a hydroformylation reaction zone. An extraction zone advantageously is employed in conjunction with the reaction zone as part of the product recovery system. Use of the amine can produce an extraction zone aqueous effluent stream with an acceptable pH range, and provides the extraction zone with acceptable buffering capacity. The pH of the extraction zone aqueous effluent stream is controlled by extracting the amine and the neutralized phosphorus acidic compound from the organic phase of the extraction zone and forming a buffered aqueous solution in situ.

All references to the Periodic Table of the Elements and the various groups therein are to the version published in the CRC Handbook of Chemistry and Physics, 72nd Ed. (1991-1992) CRC Press, at page I-10.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc. Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the term "ppmw" means part per million by weight.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds that can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy, halo, and amino. The permissible substituents can be one or more and the same or different for appropriate organic compounds. This invention is not intended to be limited in any manner by the permissible substituents of organic compounds.

As used herein, the term "hydroformylation" is contemplated to include, but is not limited to, all hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes. The aldehydes may be asymmetric or non-asymmetric.

The terms "reaction fluid," "reaction medium" and "catalyst solution" are used interchangeably herein, and may include, but are not limited to, a mixture comprising: (a) a metal-organophosphorous ligand complex catalyst, (b) free organophosphorous ligand, (c) aldehyde product formed in the reaction, (d) unreacted reactants, (e) a solvent for said metal-organophosphorous ligand complex catalyst and said free organophosphorous ligand, and, optionally, (f) one or more phosphorus acidic compounds formed in the reaction (which may be homogeneous or heterogeneous, and these compounds include those adhered to process equipment surfaces). The reaction fluid can encompass, but is not limited to, (a) a fluid in a reaction zone, (b) a fluid stream on its way to a separation zone, (c) a fluid in a separation zone, (d) a recycle stream, (e) a fluid withdrawn from a reaction zone or separation zone, (f) a withdrawn fluid being treated with an aqueous solution, (g) a treated fluid returned to a reaction zone or separation zone, (h) a fluid in an external cooler, and (i) ligand decomposition products and their salts.

For the purposes of the invention, the term "heavies" means compounds that have a boiling point higher than that of the desired aldehyde product(s).

As used herein, the term "extractor" means any suitable vessel or container, e.g., any vessel suitable for use as a liquid/liquid extractor, that provides a suitable means for thorough contact between the reaction fluid and an aqueous solution.

For the purposes of the invention, the term "extraction zone" means an equipment system that comprises at least one extractor. An extraction zone can have multiple extractors arranged in parallel, series, or both.

The term "extraction zone aqueous effluent stream" refers to an effluent stream from the extraction zone that has, as its source, an aqueous phase that results following contact of the catalyst solution with an aqueous solution in an extraction zone.

For the purposes of the invention, the term "reaction zone" mean an equipment system that comprises at least one reactor, and that feeds at least a portion of the liquid effluent to a product-catalyst separation zone, which can comprise an extraction zone. The term "first reactor" refers to the first reactor in the reaction zone.

"Hydrolyzable phosphorous ligands" are trivalent phosphorous ligands that contain at least one P—Z bond wherein Z is oxygen, nitrogen, chlorine, fluorine or bromine. Examples include, but are not limited to, phosphites, phosphino-phosphites, bisphosphites, phosphonites, bisphosphonites, phosphinites, phosphoramidites, phosphino-phosphoramidites, bisphosphoramidites, fluorophosphites, and the like. The ligands may include chelate structures and/or may contain multiple P—Z moieties such as polyphosphites, polyphosphoramidites, etc. and mixed P—Z moieties such as phosphite-phosphoramidites, flurophosphite-phosphites, and the like.

The term "complex" as used herein means a coordination compound formed by the union of one or more electronically rich molecules or atoms capable of independent existence with one or more electronically poor molecules or atoms, each of which is also capable of independent existence. For example, the organophosphorous ligands employable herein may possess one or more phosphorus donor atoms, each having one available or unshared pair of electrons that are each capable of forming a coordinate bond independently or possibly in concert (e.g., via chelation) with the metal. Carbon monoxide, which is also properly classified as a ligand, can also be present and coordinated to the metal. The ultimate composition of the complex catalyst may also contain an additional ligand, e.g., hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, e.g., the alkyl or aryl), acetate, acetylacetonate, $SO_4$, $PF_4$, $PF_6$, $NO_2$, $NO_3$, $CH_3$, $CH_2=CHCH_2$, $CH_3CH=CHCH_2$, $C_6H_5CN$, $CH_3CN$, $NH_3$, pyridine, $(C_2H_5)_3N$, mono-olefins, diolefins and triolefins, tetrahydrofuran, and the like. The complex species are preferably free of any additional organic ligand or anion that might poison the catalyst or have an undue adverse effect on catalyst performance. It is preferred in the metal-organophosphite ligand complex catalyzed hydroformylation reactions that the active catalysts be free of halogen and sulfur directly bonded to the metal, although such may not be absolutely necessary.

The number of available coordination sites on the transition metal is well known in the art and depends upon the particular transition metal selected. The catalytic species may comprise a complex catalyst mixture of monomeric, dimeric or higher nuclearity forms, which forms preferably are characterized by at least one organophosphorus-containing molecule complexed per one molecule of metal, for example, rhodium. For instance, it is considered that the catalytic species of the preferred catalyst employed in the hydroformylation reaction may be complexed with carbon monoxide and hydrogen in addition to one or more organophosphorous ligand(s).

It is recognized that the term "pH" is properly defined only for aqueous systems. When the term "effective pH" is used in this disclosure, it refers to the pH of an aqueous extraction of an organic phase to represent the amount of acidity/alkalinity present in that organic phase.

Buffers are mixtures of acids and bases. For the purposes of the invention, a buffer is an aqueous solution consisting of a mixture of a weak acid and its conjugate base or a weak base and its conjugate acid.

The water-soluble amine is employed in an amount sufficient to maintain the pH of the extraction zone aqueous effluent stream at the desired value. Advantageously, the amine is employed in a positive amount that is not more than 0.075 mmole/liter of reaction fluid, preferably not more than 0.05 mmole/liter, and even more preferably not more than 0.030 mmole/liter, as measured in the reaction fluid in the reaction zone. Advantageously, the amount of amine employed is an amount that is at least 0.005 mmole/liter of reaction fluid, preferably at least 0.015 mmole/liter, and even more preferably at least 0.025 mmole/liter. Advantageously, the amine is employed in an amount that is from 0.005 to 0.075 mmole/liter of reaction fluid, preferably from 0.015 to 0.05 mmole/liter, and even more preferably from 0.025 to 0.030 mmole/liter. Mixtures of amines can be employed. The concentration of the amine in the reaction fluid in the reaction zone can be measured by conventional techniques well-known to those skilled in the art including, for example, gas chromatography and liquid chromatography.

Advantageously, the water-soluble amine has the following two properties: 1) it is weakly basic in order to avoid heavies formation in the reaction zone; and 2) it is water-soluble to avoid accumulation in the reaction fluid. The alkalinity or basicity of the water-soluble amine is generally reported as the pKa of the conjugate acid, which advantageously is from 5 to 11 at the temperature of the extraction zone. The pKa is preferably from 6.0 to 9.5 and most preferably is from 6.5 to 9.0. Candidates for the amine can be tested for heavies formation by heating the product aldehyde with the amine at elevated temperature. Acceptable amines will exhibit less than 1 gram of heavies formation per liter of test solution per day at hydroformylation temperatures. The amount of heavies formation can be readily determined by gas or liquid chromatography, as is known to those skilled in the art. The amine advantageously is selected from one or more of the following classes.

One class of amine has the structure:

(IX)

wherein $R^{32}$, $R^{33}$, and $R^{34}$ each independently represent H or alkyl or aryl substituents such that no more than one of $R^{32}$, $R^{33}$, and $R^{34}$ is hydrogen, preferably none are hydrogen, and wherein at least one is an electron withdrawing substituent and preferably at least 2 are electron withdrawing substituents. The electron withdrawing alkyl or aryl substituents include alkyl-substituted or unsubstituted aryl, halogenated, alkoxylated, alkylalkoxylated, or carboxylated aryl groups, beta-alkoxy or beta-alkoxyalkyls (such as beta-hydroxyethyl, beta-hydroxy-alpha-methylethyl, beta-hydroxy-beta-methylethyl and ethoxylated and/or propoxylated adducts thereof). Examples of preferred amines of this class include triethanolamine, methyldiethanolamine, ethyldiethanolamine, dimethylethanolamine and tri(2-hydroxypropyl)amine and ethoxylates thereof.

Another class of amine has the structure shown in formula (X):

(X)

wherein each $R^{36}$ independently represents $C_1$-$C_4$ alkyl, hydroxyl (and ethoxylated and/or propoxylated adducts thereof), alkylalkoxy, or halogen, x is 1-3 and z is 0-6. Preferably, multiple $R^{36}$ moieties are present that may be different and, most preferably, several are located on each side of the nitrogen moiety. Preferred examples are 4-hydroxyl-2,2,6,6-tetramethylpiperidine and its derivatives.

Another class of suitable amines are the pyridines and related cyclic structures as shown in formula (XI), where $R^{36}$ is as defined above and q is 0-5.

(XI)

Preferably, at least one $R^{36}$ is not H, and more preferably the non-H substituent is in the ortho position. Even more preferably, non-H substituents are in both ortho-positions.

Another class of suitable weakly basic amines includes imidazoles, pyrazoles, indazoles, 1,2,3-triazoles, 1,2,4-triazoles, 2,1,3-triazoles, 4, 1,2-triazoles, 1,2-diazines, 1,3-diazines, 1,4-diazines, 1,3,5-triazines, and benzimidazoles that have substituents, such as those described for $R^{32}$, that increase water solubility to meet the water-catalyst solution partitioning requirement described hereinbelow. Examples of these amines are described in U.S. Pat. No. 7,351,339 and copending U.S. provisional patent application Ser. No. 61/790,642, filed Mar. 15, 2013.

For the purposes of the invention, the term "water solubility" of the amine is determined as the ratio of the solubility between the aqueous phase in the extraction zone and the organic catalyst solution phase in the extraction zone, and advantageously is at least 2:1, preferably at least 100:1, and most preferably at least 200:1. This can be determined by adding the amine to a 1:1 mixture of water and catalyst solution, mixing, letting the two phases separate then analyzing the two layers to determine the concentration in the two phases by conventional means such as gas chromatography, as is known to those skilled in the art. These amines are polar amines wherein the polar moieties (generally electron-withdrawing moieties) enhance water solubility and reduce the basicity of the amine function.

The hydroformylation process, and conditions for its operation, are well known. Conducting a hydroformylation reaction involves contacting in a reaction zone CO, $H_2$, and at least one olefin in the presence of a hydroformylation catalyst under hydroformylation conditions sufficient to form at least one aldehyde product. The catalyst comprises as components a transition metal and a hydrolyzable organophosphorous ligand. Optional components for addition to the reaction zone include an epoxide and/or water.

Hydrogen and carbon monoxide may be obtained from any suitable source, including petroleum cracking and refinery operations. Syngas mixtures are a preferred source of hydrogen and CO.

Syngas (from synthesis gas) is the name given to a gas mixture that contains varying amounts of CO and $H_2$. Production methods are well known. Hydrogen and CO typically are the main components of syngas, but syngas may contain $CO_2$ and inert gases such as $N_2 CH_4$, and Ar. The ratio of $H_2$ to CO varies greatly but generally ranges from 1:100 to 100:1 and preferably between 1:10 and 10:1. Syngas is commercially available and is often used as a fuel source or as an intermediate for the production of other chemicals. The most preferred $H_2$:CO ratio for chemical production is between 3:1 and 1:3 and usually is targeted to be between about 1:2 and 2:1 for most hydroformylation applications.

The substituted or unsubstituted olefinic unsaturated reactants that may be employed in the hydroformylation process include both optically active (prochiral and chiral) and non-optically active (achiral) olefinic unsaturated compounds containing from 2 to 40, preferably 3 to 20, carbon atoms. These compounds are described in detail in US 2010/006980. Such olefinic unsaturated compounds can be terminally or internally unsaturated and be of straight-chain, branched chain or cyclic structures, as well as olefin mixtures, such as obtained from the oligomerization of propene, butene, isobutene, etc. (such as so called dimeric, trimeric or tetrameric propylene and the like, as disclosed, for example, in U.S. Pat. Nos. 4,518,809 and 4,528,403).

A solvent advantageously is employed in the hydroformylation process. Any suitable solvent that does not unduly interfere with the hydroformylation process can be used. By way of illustration, suitable solvents for rhodium catalyzed hydroformylation processes include those disclosed, for example, in U.S. Pat. Nos. 3,527,809; 4,148,830; 5,312,996; and 5,929,289. Non-limiting examples of suitable solvents include saturated hydrocarbons (alkanes), aromatic hydrocarbons, water, ethers, polyethers, aldehydes, ketones, nitriles, alcohols, esters, and aldehyde condensation products. Specific examples of solvents include: tetraglyme, pentanes, cyclohexane, heptanes, benzene, xylene, toluene, diethyl ether, tetrahydrofuran, butyraldehyde, and benzonitrile. The organic solvent may also contain dissolved water up to the saturation limit. Illustrative preferred solvents include ketones (e.g., acetone and methylethyl ketone), esters (e.g., ethyl acetate, di-2-ethylhexyl phthalate, 2,2,4-trimethyl-1,3-pentanediol monoisobutyrate), hydrocarbons (e.g., toluene), nitrohydrocarbons (e.g., nitrobenzene), ethers (e.g., tetrahydrofuran (THF)) and sulfolane. In rhodium catalyzed hydroformylation processes, it may be preferred to employ, as a primary solvent, aldehyde compounds corresponding to the aldehyde products desired to be produced and/or higher boiling aldehyde liquid condensation by-products, for example, as might be produced in situ during the hydroformylation process, as described for example in U.S. Pat. No. 4,148,380 and U.S. Pat. No. 4,247,486. The primary solvent will normally eventually additionally comprise both aldehyde products and heavies, due to the nature of the continuous process. The amount of solvent is not especially critical and need only be sufficient to provide the reaction medium with the desired amount of transition metal concentration. Typically, the amount of solvent ranges from about 5 percent to about 95 percent by weight, based on the total weight of the reaction fluid. Mixtures of solvents may be employed.

Illustrative metal-organophosphorous ligand complexes employable in such hydroformylation reactions include metal-organophosphorous ligand complex catalysts. These catalysts, as well as methods for their preparation, are well known in the art and include those disclosed in the patents mentioned herein. In general, such catalysts may be pre-formed or formed in situ and comprise metal in complex combination with an organophosphorous ligand, carbon monoxide and optionally hydrogen. The ligand complex species may be present in mononuclear, dinuclear and/or higher nuclearity forms. However, the exact structure of the catalyst is not known.

The metal-organophosphorous ligand complex catalyst can be optically active or non-optically active. The metals can include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. Mixtures of these metals may be used. The permissible organophosphorous ligands that make up the metal-organophosphorous ligand complexes and free organophosphorous ligand include mono-, di-, tri- and higher polyorganophosphorus ligands. Mixtures of ligands may be employed in the metal-organophosphorous ligand complex catalyst and/or free ligand, and such mixtures may be the same or different.

The organophosphorous compounds that may serve as the ligand of the metal-organophosphorous ligand complex catalyst and/or free ligand may be of the achiral (optically inactive) or chiral (optically active) type and are well known in the art. Achiral organophosphorous ligands are preferred.

Among the organophosphorous ligands that may serve as the ligand of the metal-organophosphorous ligand complex catalyst are monoorganophosphite, diorganophosphite, triorganophosphite and organopolyphosphite compounds. Such organophosphorous ligands and methods for their preparation are well known in the art.

Representative monoorganophosphites may include those having the formula:

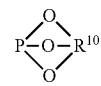

<<I>> wherein $R^{10}$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane and the like. Such monoorganophosphites may be found described in greater detail, for example, in U.S. Pat. No. 4,567,306.

Representative diorganophosphites may include those having the formula:

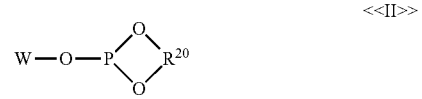

<<II>> wherein $R^{20}$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above Formula (II) include alkyl and aryl radicals, while representative substituted and unsubstituted divalent hydrocarbon radicals represented by $R^{20}$ include divalent acyclic radicals and divalent aromatic radicals. Illustrative divalent acyclic radicals include, for example, alkylene, alkylene-oxy-alkylene, alkylene-S-alkylene, cycloalkylene radicals, and, alkylene-$NR^{24}$-alkylene wherein $R^{24}$ is hydrogen or a substituted or unsubstituted monovalent hydrocarbon radical, e.g., an alkyl radical having 1 to 4 carbon atoms. The more preferred divalent acyclic radicals are the divalent alkylene radicals such as disclosed more fully, for example, in U.S. Pat. Nos. 3,415,906 and 4,567,302 and the like. Illustrative divalent aromatic radicals include, for example, arylene, bisarylene, arylene-alkylene, arylene-alkylene-arylene, arylene-oxy-arylene, arylene-NR$^{24}$-arylene wherein R$^{24}$ is as defined above, arylene-S-arylene, arylene-S-alkylene and the like. More preferably R$^{20}$ is a divalent aromatic radical such as disclosed more fully, for example, in U.S. Pat. Nos. 4,599,206, 4,717,775, 4,835,299, and the like.

Representative of a more preferred class of diorganophosphites are those of the formula:

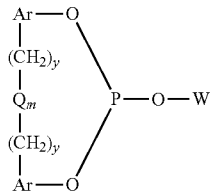
<<III>> wherein W is as defined above, each Ar is the same or different and represents a substituted or unsubstituted aryl radical, each y is the same or different and is a value of 0 or 1, Q represents a divalent bridging group selected from —C(R$^{33}$)$_2$—, —O—, —S—, —NR$^{24}$—, Si(R$^{35}$)$_2$ and —CO—, wherein each R$^{33}$ is the same or different and represents hydrogen, an alkyl radical having from 1 to 12 carbon atoms, phenyl, tolyl, and anisyl, R$^{24}$ is as defined above, each R$^{35}$ is the same or different and represents hydrogen or a methyl radical, and m has a value of 0 or 1. Such diorganophosphites are described in greater detail, for example, in U.S. Pat. Nos. 4,599,206; 4,717,775; and 4,835,299.

Representative triorganophosphites may include those having the formula:

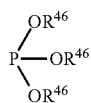
<<IV>> wherein each R$^{46}$ is the same or different and is a substituted or unsubstituted monovalent hydrocarbon radical e.g., an alkyl, cycloalkyl, aryl, alkaryl and aralkyl radicals that may contain from 1 to 24 carbon atoms. Illustrative triorganophosphites include, for example, trialkyl phosphites, dialkylaryl phosphites, alkyldiaryl phosphites, triaryl phosphites, and the like, such as, for example, trimethyl phosphite, triethyl phosphite, butyldiethyl phosphite, dimethylphenyl phosphite, triphenyl phosphite, trinaphthyl phosphite, bis(3,6,8-tri-t-butyl-2-naphthyl)methylphosphite, bis(3,6,8-tri-t-butyl-2-naphthyl)cyclohexylphosphite, tris(3,6-di-t-butyl-2-naphthyl)phosphite, bis(3,6,8-tri-t-butyl-2-naphthyl)phenylphosphite, and bis(3,6,8-tri-t-butyl-2-naphthyl)(4-sulfonylphenyl)phosphite, and the like. The most preferred triorganophosphite is triphenylphosphite. Such triorganophosphites are described in greater detail, for example, in U.S. Pat. Nos. 3,527,809 and 5,277,532.

Representative organopolyphosphites contain two or more tertiary (trivalent) phosphorus atoms and may include those having the formula:

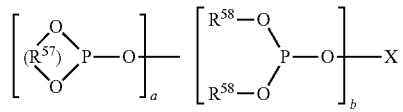
<<V>> wherein X represents a substituted or unsubstituted n-valent organic bridging radical containing from 2 to 40 carbon atoms, each R$^{57}$ is the same or different and represents a divalent organic radical containing from 4 to 40 carbon atoms, each R$^{58}$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. It is to be understood that when a has a value of 2 or more, each R$^{57}$ radical may be the same or different. Each R$^{58}$ radical may also be the same or different in any given compound.

Representative n-valent (preferably divalent) organic bridging radicals represented by X and representative divalent organic radicals represented by R$^{57}$ above, include both acyclic radicals and aromatic radicals, such as alkylene, alkylene-Q$_m$-alkylene, cycloalkylene, arylene, bisarylene, arylene-alkylene, and arylene-(CH$_2$)$_y$-Q$_m$-(CH$_2$)$_y$-arylene radicals, and the like, wherein each Q, y and m are as defined above in Formula (III). The more preferred acyclic radicals represented by X and R$^{57}$ above are divalent alkylene radicals, while the more preferred aromatic radicals represented by X and R$^{57}$ above are divalent arylene and bisarylene radicals, such as disclosed more fully, for example, in U.S. Pat. Nos. 4,769,498; 4,774,361: 4,885,401; 5,179,055; 5,113,022; 5,202,297; 5,235,113; 5,264,616 and 5,364,950, and 5,527,950. Representative preferred monovalent hydrocarbon radicals represented by each R$^{58}$ radical above include alkyl and aromatic radicals.

Illustrative preferred organopolyphosphites may include bisphosphites such as those of Formulas (VI) to (VIII) below:

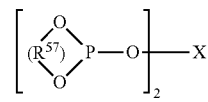
<<VI>>

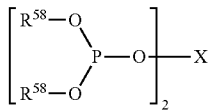
<<VII>>

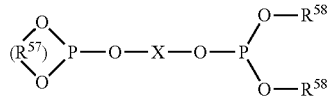
<<VIII>> wherein each R$^{57}$, R$^{58}$ and X of Formulas (VI) to (VIII) are the same as defined above for Formula (V). Preferably each R$^{57}$ and X represents a divalent hydrocarbon radical selected from alkylene, arylene, arylene-alkylene-arylene, and bisarylene, while each R$^{58}$ radical represents a monovalent hydrocarbon radical selected from alkyl and aryl radicals. Organophosphite ligands of such Formulas (V) to (VIII) may be found disclosed, for example, in U.S. Pat. Nos. 4,668,651; 4,748,261; 4,769,498; 4,774,361; 4,885, 401; 5,113,022; 5,179,055; 5,202,297; 5,235,113; 5,254,741; 5,264,616; 5,312,996; 5,364,950; and 5,391,801.

Specific illustrative examples of such organophosphite ligands include the following: 2-t-butyl-4-methoxyphenyl(3,3'-di-t-butyl-5,5'-dimethoxy-1,1'-biphenyl-2,2'-diyl)phosphite, methyl(3,3'-di-t-butyl-5,5'-dimethoxy-1,1'-biphenyl-2,2'-diyl)phosphite, 6,6'-[[3,3'-bis(1,1-dimethylethyl)-5,5'-dimethoxy-[1,1'-biphenyl]-2,2'-diyl]bis(oxy)]bis-dibenzo[d,f][1,3,2]dioxaphosphepin, 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepin, (2R,4R)-di[2,2'-(3,3',5,5'-tetrakis-tert-butyl-1,1-biphenyl)]-2,4-pentyldiphosphite, (2R,4R)di[2,2'-(3,3'-di-tert-butyl-5,5'-dimethoxy-1,1'-biphenyl)]-2,4-pentyldiphosphite, 2-[[2-[[4,8-bis(1,1-dimethylethyl), 2,10-dimethoxydibenzo-[d,f][1,3,2]dioxophosphepin-6-yl]oxy]-3-(1,1-dimethylethyl)-5-methoxyphenyl]methyl]-4-methoxy, methylenedi-2,1-phenylene tetrakis[2,4-bis(1,1-dimethylethyl)phenyl]ester of phosphorous acid, and [1,1'-biphenyl]-2,2'-diyl tetrakis [2-(1,1-dimethylethyl)-4-methoxyphenyl]ester of phosphorous acid.

The metal-organophosphorous ligand complex catalysts may be in homogeneous or heterogeneous form. For instance, preformed rhodium hydrido-carbonyl-organophosphorous ligand catalysts may be prepared and introduced into a hydroformylation reaction mixture. More preferably, the rhodium-organophosphorous ligand complex catalysts can be derived from a rhodium catalyst precursor that may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$, and the like may be introduced into the reaction mixture along with the organophosphorous ligand for the in situ formation of the active catalyst. In a preferred embodiment, rhodium dicarbonyl acetylacetonate is employed as a rhodium precursor and reacted in the presence of a solvent with the organophosphorous ligand to form a catalytic rhodium-organophosphorous ligand complex precursor that is introduced into the reactor along with excess (free) organophosphorous ligand for the in situ formation of the active catalyst. In any event, it is sufficient that carbon monoxide, hydrogen and the organophosphorous ligand are all ligands that are capable of being complexed with the metal and that an active metal-organophosphorous ligand catalyst is present in the reaction mixture under the conditions used in the hydroformylation reaction. Carbonyl and organophosphorous ligands may be complexed to the rhodium either prior to, or in situ during, the hydroformylation process.

By way of illustration, a preferred catalyst precursor composition consists essentially of a solubilized rhodium carbonyl organophosphite ligand complex precursor, a solvent and, optionally, free organophosphite ligand. The preferred catalyst precursor composition can be prepared by forming a solution of rhodium dicarbonyl acetylacetonate, an organic solvent and a organophosphite ligand. The organophosphorous ligand readily replaces one of the carbonyl ligands of the rhodium acetylacetonate complex precursor as witnessed by the evolution of carbon monoxide gas.

Accordingly, the metal-organophosphorus ligand complex catalyst advantageously comprise the metal complexed with carbon monoxide and an organophosphorous ligand, said ligand being bonded (complexed) to the metal in a chelated and/or non-chelated fashion.

Mixtures of catalysts can be employed. The amount of metal-organophosphorous ligand complex catalyst present in the reaction fluid need only be that minimum amount necessary to provide the given metal concentration desired to be employed and that will furnish the basis for at least the catalytic amount of metal necessary to catalyze the particular hydroformylation process involved such as disclosed, for example, in the above-mentioned patents. In general, catalytic metal, e.g., rhodium, concentrations in the range of from 10 ppmw to 1000 ppmw, calculated as free metal in the reaction medium, should be sufficient for most processes, while it is generally preferred to employ from 10 to 500 ppmw of metal, and more preferably from 25 to 350 ppmw of metal.

In addition to the metal-organophosphorous ligand complex catalyst, free organophosphorous ligand (i.e., ligand that is not complexed with the metal) may also be present in the reaction medium. The free organophosphorous ligand may correspond to any of the above-defined organophosphorous ligands discussed above. It is preferred that the free organophosphorous ligand be the same as the organophosphorous ligand of the metal-organophosphorous ligand complex catalyst employed. However, such ligands need not be the same in any given process. The hydroformylation process of this invention may involve from 0.1 moles or less to 100 moles or higher of free organophosphorous ligand per mole of metal in the reaction medium. Preferably, the hydroformylation process is carried out in the presence of from 1 to 50 moles of organophosphorous ligand per mole of metal present in the reaction medium. More preferably, for organopolyphosphites, from 1.1 to 4 moles of organopolyphosphite ligand are employed per mole of metal. Said amounts of organophosphorous ligand are the sum of both the amount of organophosphorous ligand that is bound (complexed) to the metal present and the amount of free organophosphorous ligand present. If desired, additional organophosphorous ligand can be supplied to the reaction medium of the hydroformylation process at any time and in any suitable manner, e.g., to maintain a predetermined level of free ligand in the reaction medium.

In one embodiment, the rhodium catalyst may be impregnated onto any solid support, such as inorganic oxides, (i.e., alumina, silica, titania, or zirconia) carbon, membranes, thin films, or ion exchange resins, supported on, or intercalated inside the pores of, a zeolite, glass or clay, insoluble polymer support, or may also be dissolved in a liquid film coating the pores of said zeolite or glass.

Illustrative metal-organophosphorous ligand complex catalyzed hydroformylation processes that may experience hydrolytic degradation include those processes as described, for example, in U.S. Pat. Nos. 4,148,830; 4,593,127; 4,769,498; 4,717,775; 4,774,361; 4,885,401; 5,264,616; 5,288,918; 5,360,938; 5,364,950; 5,491,266 and 7,196,230. Species containing the P—Z moiety that will likely undergo hydrolytic degradation include organophosphonites, phosphoramidites, and fluorophosphonites such as described WO 2008/071508, WO 2005/042458, and U.S. Pat. Nos. 5,710,344, 6,265,620, 6,440,891, 7,009,068, 7,145,042, 7,586,010, 7,674,937, and 7,872,156. Accordingly, the hydroformylation processing techniques that are advantageously employed may correspond to any known processing techniques such as, for example, gas recycle, liquid recycle, and combinations thereof. Preferred hydroformylation processes are those involving catalyst liquid recycle.

In one embodiment of the invention, substantially no metal salt buffer is added to the process. In one embodiment of the invention, substantially no sodium-based oxy-acid buffer is added to the process.

The process of the invention employs an aqueous extraction step together with the addition of low levels of a water-soluble but relatively weak basic amine. One function of the amine is to neutralize acidic impurities. The neutralized acids are salts, e.g., ammonium salts. It is desirable to remove these salts to prevent their accumulation, which can lead to fouling and side reactions of the salts. The preferred route to remove the excess amine additive and neutralized acidic species is via an extractor in which a reaction fluid and an aqueous phase are brought together. In one embodiment of the invention, filtration and ion exchange resins, such as taught in U.S. Pat. No. 7,495,134; U.S. Pat. No. 6,153,800; and U.S. Pat. No. 8,110,709, also can be used to remove at least a portion of the salts.

The amine advantageously may serve at least one of the following two functions: 1) it may neutralize acids, e.g. in the reaction zone, to mitigate ligand and catalyst degradation; and 2) it may control pH in the extraction step. The extraction step advantageously may serve at least one of the following three functions: 1) removing the neutralized acidic species (either as the salt or the acid) from the system, 2) providing water for poisoning phosphite degradation, and 3) removing excess amine to prevent amine buildup in order to avoid excessive heavies formation. The combination of the three features provides a self-balancing system where extremes of effective pH and heavies formation are avoided while still allowing controlled poisoning phosphite hydrolysis.

The amine may be added to the process at essentially any point so long as the desired concentration of amine is achieved. For example, the amine advantageously is added to the process in at least one of the reaction zone and/or the extraction zone. In one embodiment, the water-soluble amine is added to the process in more than one location. In one embodiment of the invention, the amine is added to the water feed to the extraction zone. In one embodiment of the invention, the amine is added to the first reactor. The water-soluble amine can be the same or different at the two addition points.

In one embodiment of the invention, the amine is primarily or entirely added to the reaction zone, and the rate of adding the water-soluble amine to the reaction fluid in the reaction zone is varied to control the pH of the extraction zone aqueous effluent stream in order to control the acidity of the reaction zone. In another embodiment of the invention, the amine is primarily added to the extraction zone, and the rate of addition of the water-soluble amine to the extraction zone is varied to control the pH of the extraction zone aqueous effluent stream. In one embodiment of the invention, the amine is introduced to the extraction zone as part of the aqueous feed stream. An amine/ammonium buffer is formed in situ as acid is delivered to the extraction zone via the organic phase, e.g. the reaction fluid from the reaction zone.

The amine advantageously is removed from the process with the water phase that exits the extraction zone. Thus, additional amine must be added to the process to maintain the desired concentration of the amine. The amount of the amine to add can be determined by observing the pH in the aqueous extraction zone, such as by measuring the pH of the aqueous stream leaving the extraction zone, e.g. the extractor tails stream. Advantageously, the amount of amine being added is sufficient to maintain the pH of this extraction zone aqueous effluent stream at from 4.5 to 9.0, preferably from 5.6 to 8.0, more preferably from 6.0 to 7.5, and most preferably, from 6.3 to 7.2. Occasionally, relatively higher pH values between 7.0 and 9.0 may be employed for short periods to mitigate high ligand decomposition periods, such as during a process upset when high ligand hydrolysis is observed, but this will result in a slow buildup of poisoning phosphite if continued for prolonged periods. Alternatively, relatively lower pH values (4.5 to 6.0) may be used for short times for maximum reactivity and olefin conversion (due to minimum poisoning phosphite concentration) at the cost of higher ligand usage. This situation may be present with lower quality feed or feeds containing high levels of secondary or internal olefins that require higher reactivity catalysts to maintain production rates. This scenario would not likely be economical for long periods due to ligand degradation costs, but the ability to return to the preferred pH range rapidly simply by increasing the amine addition rate shows the flexibility of the invention. Since the amine is removed by the extractor, raising and lowering the extractor pH is easily controlled by changing the amine addition rate to the process to effect this mitigation procedure without disturbing the hydroformylation production. pH values above 9 should be avoided due to low catalyst activity (from high poisoning phosphite levels) and excessive heavies formation.

Measurement of pH can be done using any means known to those skilled in the art including, for example, by conventional titration or commercially available pH meters with proper calibration. For the purposes of the invention, it is assumed that the organic phase acidity or "effective pH" of the organic phase correlates with the observed pH of the extractor tails.

In the process of the invention, at least a portion of the water-soluble amine is removed with the aqueous layer or phase of the extraction zone and, therefore, the amine does not build up in the organic phase. Since the water-soluble amine prefers to be in the aqueous phase, it is continuously removed and does not build up in the organic layer or phase. One step of the process of the invention involves at least partially separating in an extraction zone at least one neutralized phosphorus acidic compound from the reaction fluid to form an extraction zone aqueous effluent stream and a treated hydroformylation reaction fluid. The separation involves contacting reaction fluid with an aqueous solution in the extraction zone, in which an extraction occurs. The contacting in the extraction zone not only removes free phosphorus acidic compounds from the metal-organophosphorous ligand complex catalyst-containing reaction fluid, but it also removes the neutralized phosphorus acidic compound. The treated reaction fluid can be returned to the reaction zone. The majority of the polar amine additive is removed into the water phase as the free amine or the ammonium salt in solution.

The aqueous solution fed to the extraction zone advantageously comprises a majority of water, preferably de-ionized or distilled water. The water feed may contain trace impurities, additives or preservatives, e.g., anticorrosion additives, that do not interfere with the hydroformylation catalyst. Some of these additives may have some intrinsic buffering effect, but in one embodiment of the invention they will contribute to less than 10% of the total acid neutralization performed in the extractor. As mentioned hereinabove, in one embodiment of the invention, all or part of the amine can be added to the aqueous solution feed to the extraction zone.

The manner in which the amine-containing reaction fluid from the reaction zone and the water feed are contacted in the extraction zone, as well as the amount of aqueous solution, temperature, pressure and contact time, are not narrowly critical and need only be sufficient to obtain the results desired. A decrease in one of such conditions may be compensated for by an increase in one or more of the other conditions, while the corollary is also true. In general, liquid temperatures ranging from 10° C. to 120° C., preferably from 20° C. to 80° C., and more preferably from 25° C. to 60° C., should be suitable for most instances, although lower or higher temperatures may be employed if desired. Advantageously, the contacting in the extraction zone is carried out at a pressure ranging from ambient pressure to a pressure substantially higher than the reactor pressure, and the contact time may vary from a matter of seconds or minutes to a few hours or more. In general, it is preferred to pass the reaction fluid through the aqueous solution in an extractor column in a countercurrent fashion. The column can employ sieve trays, reciprocating-plates, structured or unstructured packing, and the like.

The extraction zone aqueous effluent stream advantageously is removed from the process and can be disposed of or used according to methods known to those skilled in the art.

Success in removing phosphorus acidic compounds from the reaction fluid may be determined by measuring the rate of degradation (consumption) of the organophosphorous ligand present in the hydroformylation reaction medium. The consumption rate can vary over a wide range, e.g., from less than 0.06 up to 5 grams per liter per day, and will be governed by the desired compromise between cost of ligand and treatment frequency to keep hydrolysis below autocatalytic levels. Preferably, the aqueous extraction is carried out in such a manner that the consumption of the desired organophosphorous ligand present in the hydroformylation reaction medium is maintained at an acceptable rate, e.g., less than 0.5 grams of ligand per liter per day, and more preferably less than 0.1 grams of ligand per liter per day, and most preferably less than 0.06 grams of ligand per liter per day. As the neutralization and extraction of phosphorus acidic compounds into the aqueous solution of the extraction zone proceeds, the pH of the aqueous phase exiting the extraction zone will slowly decrease and the feed rate of water-soluble amine to the reaction zone can be increased to compensate.

The removal of at least some amount of phosphorus acidic compounds, for example, $H_3PO_3$, $H_3PO_4$, aldehyde acids such as hydroxy alkyl phosphonic acids, such as hydroxyl butyl phosphonic acid and hydroxyl pentyl phosphonic acid, and the like, from the hydroformylation system allows one to control the acidity of the hydroformylation reaction medium, thereby stabilizing the useful organophosphorous ligand by preventing or lessening its hydrolytic decomposition. Without being bound by theory, it is thought that adding the water-soluble amine to the process and allowing it to flow throughout the process enables it to neutralize the acids as they are formed. Since the water-soluble amine is available early in the process, much lower levels of amine are needed compared to the prior art, yet surprisingly very effective pH control and, thus, activity and ligand decomposition performance, are observed without detectable increases in heavies formation. If the amine is added to the extraction zone, then acid neutralization still occurs via migration of some of the amine into the organic phase and/or acid migration into the alkaline aqueous phase and the overall partition greatly favors the removal of the acidic species (either as free acid or neutralizes salt) into the aqueous phase.

In one embodiment of the invention, epoxide additives can be employed to mitigate strongly acidic impurities as taught in WO patent application filing no. PCT/US13/058714, filed Sep. 9, 2013. The epoxide additives may be added continuously or on an "as needed" basis. The resulting epoxide adduct will also be removed by the unbuffered extractor and this removal is enhanced by the presence of low levels of water-soluble amines of the invention. The preferred epoxides are water-soluble or slightly water-soluble (their solubility being increased when they react with the acidic species) such that the adducts are efficiently removed from the system, e.g. via the extraction zone aqueous effluent stream.

The hydroformylation process may be conducted in any batch, continuous or semi-continuous fashion and may involve any catalyst liquid and/or gas recycle operation desired. The particular hydroformylation process for producing aldehydes from an olefinic unsaturated compound, as well as the reaction conditions and ingredients of the hydroformylation process are not critical features of this invention.

In a preferred embodiment, the hydroformylation reaction fluid includes any fluid derived from any corresponding hydroformylation process that contains at least some amount of four different main ingredients or components, i.e., the aldehyde product, a metal-organophosphorous ligand complex catalyst, free organophosphorous ligand and a solvent for said catalyst and said free ligand. The hydroformylation reaction mixture compositions can and normally will contain additional ingredients such as those that have either been deliberately employed in the hydroformylation process or formed in situ during said process. Examples of such additional ingredients include unreacted olefin starting material, carbon monoxide and hydrogen gases, inert impurities that enter the system with the feeds, such as methane, carbon dioxide, and the like, and in situ formed by-products, such as saturated hydrocarbons and/or unreacted isomerized olefins corresponding to the olefin starting materials, ligand degradation compounds, and high boiling liquid aldehyde condensation by-products, as well as other inert co-solvent type materials or hydrocarbon additives, if employed.

The reaction conditions of the hydroformylation process may include any suitable hydroformylation conditions heretofore employed for producing optically active and/or non-optically active aldehydes. The hydroformylation reaction conditions employed will be governed by the type of aldehyde product desired. For instance, the total gas pressure of hydrogen, carbon monoxide and olefin starting compound of the hydroformylation process may range from 1 to 69,000 kPa. In general, however, it is preferred that the process be operated at a total gas pressure of hydrogen, carbon monoxide and olefin starting compound of less than 14,000 kPa and more preferably less than 3,400 kPa. The minimum total pressure is limited predominately by the amount of reactants necessary to obtain a desired rate of reaction. More specifically, the carbon monoxide partial pressure of the hydroformylation process is preferably from 1 to 6,900 kPa, and more preferably from 21 to 5,500 kPa, while the hydrogen partial pressure is preferably from 34 to 3,400 kPa and more preferably from 69 to 2,100 kPa. In general, the molar ratio of gaseous $H_2$:CO may range from 1:10 to 100:1 or higher, the more preferred molar ratio being from 1:10 to 10:1. In general, the hydroformylation process may be conducted at any operable reaction temperature. Advantageously, the hydroformylation process is conducted at a reaction temperature from −25° C. to 200° C., preferably from 50° C. to 120° C.

The hydroformylation process may be carried out using one or more suitable reactors such as, for example, a fixed bed reactor, a fluid bed reactor, a plug-flow reactor, a continuous stirred tank reactor (CSTR) or a slurry reactor. The optimum size and shape of the reactor will depend on the type of reactor used. The reaction zone employed may be a single vessel or may comprise two or more discrete vessels in series or in parallel. The reaction steps may be affected by the incremental addition of one of the starting materials to the other. Also, the reaction steps can be combined by the joint addition of the starting materials. When complete conversion is not desired or not obtainable, the starting materials can be separated from the product, for example by distillation, and the starting materials then recycled back into the reaction zone.

The extraction zone employed in this invention may be a single vessel or may comprise two or more discreet vessels. In one embodiment of the invention, a reaction vessel may be employed as an extractor, e.g. when the process is operated in batch mode.

The recycle procedure generally involves withdrawing a portion of the liquid reaction medium containing the catalyst and aldehyde product from the hydroformylation reactor, i.e., reaction zone, either continuously or intermittently, and recovering the aldehyde product therefrom by use of a composite membrane, such as disclosed in U.S. Pat. No. 5,430,194 and U.S. Pat. No. 5,681,473, or by the more conventional and preferred method of distilling it, i.e., vaporization separation, in one or more stages under normal, reduced or elevated pressure, as appropriate, in a separate distillation zone, the non-volatilized metal catalyst containing residue being recycled to the reaction zone as disclosed, for example, in U.S. Pat. No. 5,288,918. Condensation of the volatilized materials, and separation and further recovery thereof, e.g., by further distillation, can be carried out in any conventional manner, and the crude aldehyde product can be passed on for further purification and isomer separation, hydrogenation, oxidation, and/or condensation, if desired, and any recovered reactants, e.g., olefinic starting material and syngas, can be recycled in any desired manner to the hydroformylation zone (reactor). The recovered metal catalyst-containing raffinate of such membrane separation or recovered non-volatilized metal catalyst-containing residue of such vaporization separation can be recycled to the hydroformylation zone (reactor) in any conventional manner desired.

The materials of construction are not particularly critical to the invention and can readily be chosen by one of ordinary skill in the art. The hydroformylation process may be conducted in, for example, glass lined, stainless steel or similar type reaction equipment. The reaction zone may be fitted with one or more internal and/or external heat exchanger(s) in order to control undue temperature fluctuations, or to prevent any possible "runaway" reaction temperatures.

It is generally preferred to carry out the hydroformylation process in a continuous manner. Continuous hydroformylation processes are well known in the art, with or without olefin and/or catalyst recycle.

The separation zone employed may be a single vessel or may comprise two or more discrete vessels. In one embodiment, the aldehyde product mixtures may be separated from the other components of the crude reaction mixtures in which the aldehyde mixtures are produced by any suitable method such as, for example, solvent extraction, crystallization, distillation, vaporization, wiped film evaporation, falling film evaporation, phase separation, filtration, and the like or any combination thereof. It may be desired to remove the aldehyde products from the crude reaction mixture as they are formed through the use of trapping agents as described in WO 88/08835. The reaction zone(s) and separation zone(s) employed herein may exist in the same vessel or in different vessels. For example, reactive separation techniques such as reactive distillation, reactive membrane separation, and the like, may occur in the reaction zone(s). One method for separating the aldehyde mixtures from the other components of the crude reaction mixtures is by membrane separation, which is described, for example in U.S. Pat. Nos. 5,430,194 and 5,681,473.

More particularly, distillation and separation of the desired aldehyde product from the metal-organophosphorous complex catalyst containing reaction fluid may take place at any suitable temperature desired. In general, it is preferred that such distillation take place at relatively low temperatures, such as below 150° C., and more preferably at a temperature in the range of from 50° C. to 140° C. It is also generally preferred that such aldehyde distillation take place under reduced pressure, e.g., a total gas pressure that is substantially lower than the total gas pressure employed during hydroformylation when low boiling aldehydes (e.g., $C_4$ to $C_6$) are involved or under vacuum when high boiling aldehydes (e.g., $C_7$ or greater) are involved. For instance, a common practice is to subject the liquid reaction product medium removed from the hydroformylation reactor to a pressure reduction so as to volatilize a substantial portion of the unreacted gases dissolved in the liquid medium that now contains a much lower synthesis gas concentration than is present in the reaction medium to the distillation zone, e.g., vaporizer/separator, wherein the desired aldehyde product is distilled. In general, distillation pressures ranging from vacuum pressures on up to total gas pressure of 340 kPa should be sufficient for most purposes.

Illustrative non-optically active aldehyde products include e.g., propionaldehyde, n-butyraldehyde, isobutyraldehyde, n-valeraldehyde, 2-methyl 1-butyraldehyde, hexanal, hydroxyhexanal, 2-methyl 1-heptanal, nonanal, 2-methyl-1-octanal, decanal, adipaldehyde, 2-methylglutaraldehyde, 2-methyladipaldehyde, 3-hydroxypropionaldehyde, 6-hydroxyhexanal, alkenals, e.g., 2-, 3- and 4-pentenal, alkyl 5-formylvalerate, 2-methyl-1-nonanal, 2-methyl 1-decanal, 3-propyl-1-undecanal, pentadecanal, 3-propyl-1-hexadecanal, eicosanal, 2-methyl-1-tricosanal, pentacosanal, 2-methyl-1-tetracosanal, nonacosanal, 2-methyl-1-octacosanal, hentriacontanal, 2-methyl-1-triacontanal, and the like.

Illustrative optically active aldehyde products include (enantiomeric) aldehyde compounds prepared by the asymmetric hydroformylation process of this invention such as, e.g., S-2-(p-isobutylphenyl)-propionaldehyde, S-2-(6-methoxy-2-naphthyl)propionaldehyde, S-2-(3-benzoylphenyl)-propionaldehyde, S-2-(3-fluoro-4-phenyl)phenylpropionaldehyde, and S-2-(2-methylacetaldehyde)-5-benzoylthiophene.

SPECIFIC EMBODIMENTS OF THE INVENTION

All parts and percentages in the following examples are by weight unless otherwise indicated. Pressures are given as absolute pressure unless otherwise indicated.

General Procedure

A liquid recycle reactor system is employed that consists of two 1 liter stainless steel stirred tank reactors connected in series. Each reactor is equipped with a vertically mounted agitator and a circular tubular sparger located near the bottom of the reactor. Each sparger contains a plurality of holes of sufficient size to provide the desired gas flow into the liquid body in the reactor. The spargers are used for feeding the olefin and/or syngas to the reactor, and can also be used to recycle unreacted gases to each reactor. Each reactor has a silicone oil shell as a means of controlling reactor temperature. Reactors 1 to 2 are further connected via lines to transfer any unreacted gases and lines to allow a portion of the liquid solution containing aldehyde product and catalyst to be pumped from reactor 1 to reactor 2. Hence, the unreacted olefin of reactor 1 is further hydroformylated in reactor 2. Each reactor also contains a pneumatic liquid level controller for maintaining the desired liquid level. Reactor 2 has a blow-off vent for removal of unreacted gases.

A portion of the liquid reaction solution is continuously pumped from Reactor 2 to a vaporizer, which consists of a heated vessel at reduced pressure. The effluent stream from the vaporizer is sent to a gas-liquid separator located at the bottom of the vaporizer, where vaporized aldehyde is separated from the non-volatile components of the liquid reaction solution. The vaporized aldehyde product is condensed and collected in a product receiver. A pneumatic liquid level controller controls the level in the separator of non-volatile components, including catalyst solution to be recycled. The liquid effluent of the separator is sent to an extractor, where a water feed stream is contacted with the separator liquid effluent in order to remove acidic species. The extractor comprises a packed column contacting region and a phase separation zone, i.e., a decanter. In the decanter, an aqueous layer and a separate organic layer are formed. The organic layer, which contains catalyst to be recycled, is pumped from the decanter through a recycle line into Reactor 1.

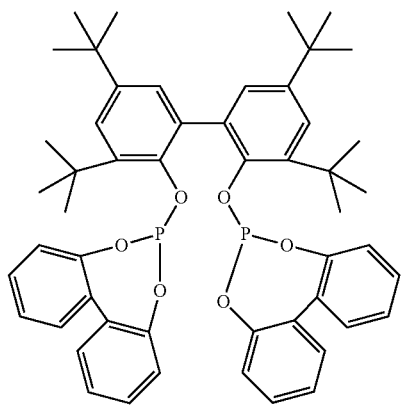

Ligand A

Comparative Experiment A (not an Embodiment of the Invention)

A hydroformylation reaction is conducted for 60 days using the General Procedure described above, except that the water feed stream is replaced with a stream consisting of a 0.04M aqueous sodium phosphate buffer solution at pH 6.8. The reactor system is charged with 2-liters of a catalyst solution comprising: (a) rhodium dicarbonyl acetylacetonate (280 ppm rhodium), (b) Ligand A (0.68 wt %; 3 molar equivalents per mole rhodium), and (c) a solvent mixture comprising 15% by weight of UCAR FILMER IBT (2,2,4-trimethyl-1,3-pentanediol monoisobutyrate), available from The Dow Chemical Company, and 85% by weight of mixed $C_5$ aldehyde (n-valeraldehyde and 2-methyl butyraldehyde in a weight ratio of about 30:1). The reactors are then heated to 75° C. under flowing carbon monoxide and hydrogen. Reactor 1 and 2 pressures are maintained at 160 and 110 psig respectively. A mixed butene olefin stream (consisting of approximately 18% 1-butene, 37% trans-2-butene, 30% cis-2-butene, 5% isobutene, and 10% n-butane) is fed to Reactor 1 at a rate of 1.74 gram moles per liter of reactor volume per hour. The vaporizer system is operated at 11 psia and 102 to 104° C.

Significant sodium levels build up in the organic layer of the decanter within 20 days (up to a measured 20 ppm). Occasional line plugging occurs.

Example 1

The procedure of C.E. A is followed for 42 days, except that no sodium phosphate buffer solution is employed and the pH of the aqueous extractor tails stream is controlled at an average value of 6.0 by feeding triethanolamine (TEA) (as a 12 wt % aqueous solution) directly into Reactor 1 via a syringe pump. The TEA is initially added at a rate of 0.002 mmoles/liter catalyst solution in reactor 1, which rate is equivalent to the estimated molar rate of acid generation from ligand decomposition. The actual acid generation from ligand decomposition is periodically measured by ion chromatography and high pressure liquid chromatography, and the TEA addition rate is adjusted appropriately.

Over the period of 42 days, the cumulative total of TEA that is fed to Reactor 1 is 20 millimoles TEA/liter of catalyst solution, which is equivalent on a molar basis to the measured total acid generation from ligand decomposition.

Excellent mass balance for the TEA is observed, based on observation of the aqueous decanter effluent. For the full 42 days, the measured ligand consumption is comparable to that of a control system operated under the same conditions using a conventional aqueous sodium phosphate buffer extractor.

During the 42 days, extensive analytical sampling and process measurements are made and comparisons are made to the process of Comparative Experiment A.

Compared to Comparative Experiment A, no detrimental effect is detected in hydroformylation rate, selectivity to normal and iso valeraldehydes, or the formation rate of ligand degradation products. Furthermore, compared to Comparative Experiment A, no new phosphorous-based chemical intermediates are detected using $^{31}P$ nuclear magnetic resonance (NMR) over the course of the hydroformylation and, surprisingly, no fouling is observed (as evidenced by no line plugging). Over the course of the hydroformylation, the TEA that is fed at the above mentioned conditions passes through to the aqueous effluent of the extractor completely as free TEA or as TEA-salts, thereby removing acidic compounds that are formed by ligand degradation. In addition, there is no increase in the sodium levels in the organic layer of the decanter.

Example 2

At the end of the 60 days of Comparative Experiment A, the sodium phosphate buffer solution stream is replaced with a feed stream of only water, and the TEA addition scheme used in Example 1 is initiated. The sodium level in the organic phase drops over time with periodic spikes as solid salts are dissolved. After 40 days of operation, the system is essentially free of sodium. This demonstrates that the use of the water-only extractor and TEA will remove salts deposited by the comparative system while still maintaining good catalyst performance without the need to shut the process down for cleaning.

Comparative Experiment B (not an Embodiment of the Invention)

The procedure of Ex. 1 is followed except that no TEA is fed to Reactor 1, and no extractor is employed. After 190 days, a catalyst solution containing over 4,000 ppm of hydroxybutylphosphonic acid (HBPA, an acidic ligand breakdown product readily measurable by ion chromatography) is extracted with two charges of water, reducing the amount of HBPA to 1,000 ppm in the organic phase. The extraction is performed in the reactor after shutting down feeds, and cooling to ambient temperature. No emulsions or rhodium loss to the water extraction layers is detected. However, this amount of residual HBPA is unacceptably high.

Comparative Experiment C (not an Embodiment of the Invention)

Treating the resulting organic phase from C.E. B with 1% aqueous triethanolamine (TEA) solution (0.2 wt % of catalyst solution, 0.12 mmol/L, pH>9.5) then doing a final water wash gives complete removal of HBPA from the organic phase. However, significant emulsion formation is observed and 1.5 ppm rhodium loss in the water wash is observed.

Comparative Experiment D (not an Embodiment of the Invention)

The resulting TEA-washed catalyst-containing organic phase from C.E. C is tested for reactivity and it is found that, due to the very high pH of the TEA aqueous wash (>9.5), the resulting catalyst solution quickly builds up poisoning phosphite, which results in an activity of only 25% compared to fresh catalyst. The effective pH of the washed catalyst solution is too high to permit the hydrolysis of the poisoning phosphite.

Comparative Experiments B-D demonstrate that application of the prior art gives unsatisfactory results. C.E. B demonstrates that simple water extraction is ineffective at removing the acids to acceptable levels. C.E. C demonstrates that while adding excess amine is effective in removing the acid, other undesirable consequences, such as rhodium loss and emulsion formation, are observed that cannot be tolerated in a commercial operation. In addition, C.E. D shows that the treated material of C.E. C exhibits undesirably low hydroformylation activity.

Example 3

The process of Example 1 is repeated except that a series of 30 day runs at different average pH values (as measured in the extractor aqueous effluent) are performed and the catalyst activity (based on ligand kinetic model values generated on fresh catalyst under the same conditions) and ligand usage rates are obtained. The average pH values are controlled by changing the TEA feed rate to Reactor 1. The relative ligand usage rates are scaled against the center point (pH 6.8), which is given a value of 1. The relationship between catalyst activity and ligand usage is shown in Table 1. Since activity and usage rate directly impact the cost of aldehyde production and are related to the average extractor pH, the desired reaction rate and ligand usage rate for a given process can be determined, and the average pH can then be selected to achieve the desired results.

TABLE 1

| pH | Catalyst Activity (% Model) | Relative Ligand Usage |
| --- | --- | --- |
| 5.6 | 75 | 1.48 |
| 6.8 | 67 | 1 |
| 7.6 | 55 | 0.625 |

Example 4

The procedure of C.E. A is followed, with the exception that no sodium phosphate buffer solution is employed and TEA (as a 700 ppmw aqueous solution; pH 9.3) is fed to the extractor at a constant rate of 12.6 g solution per hour. Over a period of 46 days, the acid resulting from ligand decomposition is periodically measured by ion chromatography, and ligand usage is calculated based on high pressure liquid chromatography analyses. The rate of ligand decomposition fluctuates; thus, the acid concentration changes, resulting in a molar ratio of TEA-to-acid of from 1.7:1 to 2.8:1 and an extractor aqueous effluent pH of from 6.4 to 7.2. A cumulative total of 66 mmoles TEA is fed to the extractor, which is equivalent on a molar basis to the measured total acid generated from ligand decomposition.

Relative to the process of Comparative Example A, no deleterious effect on ligand usage rate, hydroformylation rate, heavies formation or product selectivity is observed. Importantly, no evidence of insoluble materials in the organic layer of the decanter, such as fouling or line/filter plugging, is observed.

What is claimed is:

1. A process comprising: (1) conducting in a reaction zone a hydroformylation reaction employing a reaction fluid comprising (a) a phosphorus acidic compound, (b) a metal-organophosphorus ligand complex catalyst that comprises a metal of Group 8, 9 or 10 complexed with an organophosphorous ligand, and, optionally, (c) free organophosphorus ligand; (2) contacting at least a portion of the reaction fluid with a water-soluble amine to neutralize at least some amount of the phosphorus acidic compound and to form a neutralized phosphorus acidic compound; (3) at least partially separating in an extraction zone at least one neutralized phosphorus acidic compound from the reaction fluid; and (4) removing the neutralized phosphorus acidic compound from the extraction zone via an extraction zone aqueous effluent stream; with the proviso that the amount of amine is such that the concentration of the amine in the reaction zone is not more than 0.075 mmoles per liter of hydroformylation reaction fluid.

2. The process of claim 1 wherein the concentration of the amine in the reaction zone is a positive amount that is not more than 0.05 mmole/liter of hydroformylation reaction fluid.

3. The process of claim 1 wherein the water solubility of the amine is at least 2:1, and the basicity of the amine, determined as the pKa of the conjugate acid, is from 5 to 11 at the temperature of the extraction.

4. The process of claim 1 wherein the water solubility of the amine is at least 100:1, and the basicity of the amine, determined as the pKa of the conjugate acid, is from 6.0 to 9.5 at the temperature of the extraction.

5. The process of claim 1 wherein the water solubility of the amine is at least 200:1, and the basicity of the amine, determined as the pKa of the conjugate acid, is from 6.5 to 9.0 at the temperature of the extraction.

6. The process of claim 1 wherein the amine comprises at least one of triethanolamine, methyldiethanolamine, ethyldiethanolamine, tri(2-hydroxypropyl)amine, and ethoxylates of these.

7. The process of claim 1 wherein the amine is triethanolamine.

8. The process of claim 1 wherein the extraction zone aqueous effluent stream has a pH of from 4.5 to 9.

9. The process of claim 1 wherein the extraction zone aqueous effluent stream has a pH of from 6.0 to 7.5.

10. The process of claim 1 wherein at least a portion of the water-soluble amine is added to the reaction zone, and the pH of the extraction zone aqueous effluent stream is controlled by controlling the rate of addition of the water-soluble amine to the reaction zone.

11. The process of claim 9 wherein at least a portion of the water-soluble amine is added to the extraction zone, and the pH of the extraction zone aqueous effluent stream is controlled by controlling the rate of addition of the water-soluble amine to the extraction zone.

* * * * *